US011350866B2

(12) United States Patent
Wegberg et al.

(10) Patent No.: US 11,350,866 B2
(45) Date of Patent: Jun. 7, 2022

(54) READ-OUT CIRCUITRY FOR ACQUIRING A MULTI-CHANNEL BIOPOTENTIAL SIGNAL AND A SENSOR FOR SENSING A BIOPOTENTIAL SIGNAL

(71) Applicants: STICHTING IMEC NEDERLAND, Eindhoven (NL); IMEC VZW, Leuven (BE)

(72) Inventors: Roland Van Wegberg, Leuven (BE); Wim Sijbers, Leuven (BE)

(73) Assignees: STICHTING IMEC NEDERLAND, AE Eindhoven (NL); IMEC VZW, Leuven (BE)

( * ) Notice: Subject to any disclaimer, the term of this patent is extended or adjusted under 35 U.S.C. 154(b) by 270 days.

(21) Appl. No.: 16/710,132

(22) Filed: Dec. 11, 2019

(65) Prior Publication Data

US 2020/0187811 A1 Jun. 18, 2020

(30) Foreign Application Priority Data

Dec. 14, 2018 (EP) .................................... 18212714

(51) Int. Cl.
*A61B 5/282* (2021.01)
*A61B 5/00* (2006.01)
(Continued)

(52) U.S. Cl.
CPC ................ *A61B 5/282* (2021.01); *A61B 5/30* (2021.01); *A61B 5/6823* (2013.01); *A61B 5/6833* (2013.01); *H03F 3/45475* (2013.01)

(58) Field of Classification Search
CPC ......... A61B 5/282; A61B 5/30; A61B 5/6823; A61B 5/6833; A61B 2560/0209;
(Continued)

(56) References Cited

U.S. PATENT DOCUMENTS 4,023,565 A 5/1977 Ohlsson
5,841,308 A 11/1998 Nagata
(Continued)

FOREIGN PATENT DOCUMENTS

EP 2818103 A1 12/2014

OTHER PUBLICATIONS

Mitra et al., "A 700pW 8-Channel EEG/Contact-impedance Acquisition System for Dry-electrodes", 2012 IEEE Symposium on VLSI Circuits, Jun. 13, 2012, pp. 68-69 (Year: 2012).*
(Continued)

*Primary Examiner* — Mallika D Fairchild
*Assistant Examiner* — Shreya Anjaria
(74) *Attorney, Agent, or Firm* — Moser Taboada

(57) ABSTRACT

A read-out circuitry for acquiring a multi-channel biopotential signal, comprises: a plurality of read-out signal channels, each receiving an input signal from a unique signal electrode; a reference channel receiving a reference signal from a reference electrode; wherein each read-out signal channel and the reference channel comprises a channel amplifier connected to receive the input signal in a first input node and with an output node connected to a second input node via a channel feedback loop; wherein each signal channel amplifier comprises a capacitor between the second input nodes of the signal channel amplifier and the reference channel amplifier, and wherein each signal channel feedback loop and the reference channel feedback loop comprise a filter.

15 Claims, 5 Drawing Sheets

(51) Int. Cl.
*H03F 3/45* (2006.01)
*A61B 5/30* (2021.01)

(58) Field of Classification Search
CPC .... H03F 3/45475; H03F 3/68; H03F 3/45928; H03F 3/45968; H03F 2200/261; H03F 2203/45101; H03F 2203/45138; H03F 2203/45586; H03F 2203/45588
See application file for complete search history.

(56) References Cited

U.S. PATENT DOCUMENTS

| | | | | |
|---|---|---|---|---|
| 2014/0142458 | A1 | 5/2014 | Leyde et al. | |
| 2017/0095153 | A1* | 4/2017 | Bardy | A61B 5/364 |

OTHER PUBLICATIONS

Rijn et al., "High-quality recording of bioelectric events, Part 2 Low-noise, low-power multichannel amplifier design", Medical & Biological Engineering & Computing, 1991, vol. 29, pp. 433-440 (Year: 1991).*

Rijn et al., "High-quality recording of bioelectric events, Part 2 Low-noise, low-power multichannel amplifier design", Medical & Biological Engineering & Computing, 1991, vol. 29, pp. 433-440.

Degen et al., "An improved Method to continuously monitor the Electrode-Skin Impedance during Bioelectric Measurements", Proceedings of the 29th International Conference of the IEEE EMBS, Aug. 23-26, 2007, pp. 6294-6297.

Mitra et al., "A 700μW8-Channel EEG/Contact-impedance Acquisition System for Sry-electrodes", 2012 IEEE Symposium on VLSI Circuits, Jun. 13, 2012, pp. 68-69.

Jiawei Xu et al: "A 15-Channel Digital Active Electrode System for Multi-Parameter Biopotential Measurement", IEEE Journal of Solid-State Circuits, vol. 50, No. 9, Sep. 2015, pp. 2090-2100.

Xu et al., "A Wearable 8-Channel Adaptive-Electrode EEG/ETI Acquisition System for Body Area Networks", IEEE Journal of Solid-State Circuits, vol. 49, No. 9, Sep. 1, 2014, pp. 2005-2016.

Extended European Search Report in EP18212714.2 dated Apr. 23, 2019.

* cited by examiner

READ-OUT CIRCUITRY FOR ACQUIRING A MULTI-CHANNEL BIOPOTENTIAL SIGNAL AND A SENSOR FOR SENSING A BIOPOTENTIAL SIGNAL

CROSS-REFERENCE TO RELATED APPLICATION

The present application is based on priority claimed on European Patent Application No. 18212714.2, filed on Dec. 14, 2018, the contents of which are incorporated herein by reference.

TECHNICAL FIELD

The present inventive concept relates to a read-out circuitry for acquiring a multi-channel biopotential signal. The present inventive concept also relates to a sensor for sensing a biopotential signal.

BACKGROUND

For certain biopotential signals, recording a biopotential in multiple channels is important. For instance, for acquiring of an electroencephalogram (EEG) or an electrocardiogram (ECG), multiple channels may need to be acquired in order to enable sufficient analysis of the biopotential signals.

Like trends in many technological areas, it is of interest to reduce size of sensors for sensing a biopotential signal. Providing a small-size sensor may be facilitate general handing of the sensor. Also, it may improve experience for a subject to wearing the sensor. For instance, a sensor being integrated in a small patch may imply that the sensor is arranged on a small surface area of skin of the subject, such that wearing the sensor may not affect the subject (e.g. if the sensor is to be worn for acquiring biopotential signals over an extended period of time).

When providing a small-size sensor, it may be important to control power consumption of the sensor. For instance, if the sensor is battery-powered, a limited power consumption may ensure that battery lifetime is increased or that a smaller size battery may be included in the sensor.

In A. C. Metting van Rijn et al: "High-quality recording of bioelectric events, Part 2 Low-noise, low-power multi-channel amplifier design", Medical & Biological Engineering & Computing, 1991, vol. 29, pages 433-440, a design of a multichannel instrumentation amplifier for monopolar measurements is disclosed. The amplifier has one inverting (reference) input and a number of noninverting inputs. When compared to n independent one-channel amplifiers, the multichannel design offers a considerable reduction in the number of parts while the power consumption is reduced by approximately 40 percent.

However, with the multichannel instrumentation amplifier design, input sections influence voltage at a point $P_{av}$ shared by the channels. Therefore, a badly functioning electrode may cause the amplifier not to function properly. In order to handle badly functioning electrodes, an extra common-mode sense electrode is used. This may result in a reduction of common-mode rejection ratio.

SUMMARY

An objective of the present inventive concept is to provide a read-out circuitry for acquiring a multi-channel biopotential signal with a limited power consumption. Another objective of the present inventive concept is to provide a read-out circuitry for acquiring a multi-channel biopotential signal with a high common-mode rejection ratio for the channels.

These and other objectives of the invention are at least partly met by the invention as defined in the independent claims. Preferred embodiments are set out in the dependent claims.

According to a first aspect, there is provided a read-out circuitry for acquiring a multi-channel biopotential signal, said read-out circuitry comprising: a plurality of read-out signal channels, wherein each signal channel is configured to receive an input signal from a unique signal electrode; a reference channel, which is configured to receive a reference signal from a reference electrode; wherein each of the read-out signal channels comprises a signal channel amplifier having a first input node and a second input node and an output node, wherein the first input node of the signal channel amplifier is connected to receive the input signal from the signal electrode, and wherein the output node of the signal channel amplifier is connected to the second input node of the signal channel amplifier via a signal channel feedback loop; wherein the reference channel comprises a reference channel amplifier having a first input node and a second input node and an output node, wherein the first input node of the reference channel amplifier is connected to receive the input signal from the reference electrode, and wherein the output node of the reference channel amplifier is connected to the second input node of the reference channel amplifier via a reference channel feedback loop; wherein the second input node of each signal channel amplifier is connected to the second input node of the reference channel amplifier for providing a differential input to each signal channel amplifier and for sharing amplification of the reference signal between the signal channels; wherein each signal channel amplifier comprises a capacitor between the second input node of the signal channel amplifier and the second input node of the reference channel amplifier, and wherein each signal channel feedback loop and the reference channel feedback loop comprise a filter; and wherein each read-out signal channel comprises a first output connected to the output node of the signal channel amplifier and a second output connected to the output node of the reference channel amplifier for providing a differential output by each read-out signal channel.

The read-out circuitry is configured such that the second input node of each signal channel amplifier is connected to the second input node of the reference channel amplifier. Thus, the amplification of the reference signal is shared between signal channels, which implies that only a single amplifier for amplifying the reference channel need be provided in the read-out circuitry. This implies that the read-out circuitry may provide a low power consumption and may be area efficient.

A capacitor is provided between the input nodes of the signal channel amplifier and the reference channel amplifier. Thus, the read-out circuitry enables a channel to be configured to provide a first low pass filter characteristic with a first cut-off frequency in respect of differential mode signals of the input signal of the signal channel and the reference signal and a second low pass filter characteristic with a second cut-off frequency in respect of common mode signals of the input signal of the signal channel and the reference signal.

The low pass filter in the feedback loop may provide a high pass filter function of the amplifier. The low pass filter for differential mode signals may be configured to pass the differential DC component of the signal channel and the reference channel to enable DC offset cancellation. The low pass filter for common mode signals enables common mode aggressors to be suppressed without affecting differential mode signals at the same frequency, to enable the read-out circuitry to be provided with a high common mode rejection.

The capacitor between the input nodes of the signal channel amplifier and the reference channel amplifier may be used to define a cut-off frequency for differential signals. The capacitor may have no effect on the common mode signals. Thus, the arrangement of a filter in the signal channel feedback and the reference channel feedback loop allows for different cut-off frequencies for differential mode signals and common mode signals.

Further, the reference channel is re-used and the second input node of each signal channel amplifier is connected to the second input node of the reference channel amplifier for sharing input from the reference channel. This implies that amplification of the reference signal may be made in the reference channel and that a single amplifier may be used for amplifying the reference signal, while the reference signal is used for each of the signal channels. Hence, there is no need for amplifying the same reference signal in plural amplifiers, such that a number of components of the read-out circuitry may be limited and, also, power consumption of the read-out circuitry may be limited.

Further, each signal channel may be configured to provide a differential output such that a fully differential amplifier is provided for each channel.

According to an embodiment, the read-out circuitry further comprises a buffer associated with the reference channel.

The buffer may ensure that a low impedance node may be provided in connecting the reference channel to the signal channels. This may ensure that cross-talk between channels is prevented so as to improve isolation between different signal channels.

According to an embodiment, the buffer is implemented as an operational amplifier.

An operational amplifier may be particularly suitable for providing a buffer function.

A unity gain operational amplifier may provide a high input impedance and a low output impedance, while providing an output voltage equal to an input voltage. Thus, the buffer operational amplifier may prevent cross-talk between channels.

According to an embodiment, the buffer is arranged within the reference channel feedback loop.

This implies a low impedance is provided to the capacitors between the second input node of the signal channel amplifier and the second input node of the reference channel amplifier.

According to an alternative embodiment, the buffer is arranged between the second input node of the reference channel amplifier and the capacitors of the signal channel amplifiers.

Hence, instead of arranging the buffer within the feedback loop, the buffer may be arranged outside the feedback loop. The buffer may still provide a low impedance to the capacitors between the second input node of the signal channel amplifier and the second input node of the reference channel amplifier.

According to another alternative embodiment, the buffer is arranged between the first input node of the reference channel amplifier and the capacitors of the signal channel amplifiers.

The buffer may thus provide a low impedance to the capacitors between the second input node of the signal channel amplifier and the second input node of the reference channel amplifier, by the buffer being arranged between the first input node of the reference channel amplifiers and the capacitors.

In the other alternative embodiment, the second input node of the reference channel amplifier may be connected to an output node of the buffer via a capacitor.

Since the first input node of the reference channel amplifier in the other alternative embodiment is connected to the capacitors of the signal channel amplifiers, the second input node of the reference channel amplifier may not be directly coupled to the capacitors and a capacitor may need to be arranged between the second input node of the reference channel amplifier and the output node of the buffer.

According to an embodiment, the filter of each signal channel and reference channel feedback loop is a low pass filter having a first cut-off frequency in respect of a differential signal of the input signal of the read-out signal channel and the reference signal, and wherein each signal channel and reference channel feedback loop is an active low pass filter having a second cut-off frequency in respect of a common mode signal of the input signals of the read-out signal channels and the reference signal.

By providing a low pass filter function in a feedback loop, the amplifier may have a high pass filter function. The low pass filter function for differential mode signals may be configured for passing essentially only the differential DC component, and thereby enables the DC offset between inputs to be cancelled. The low pass filter function for common mode signals may be configured for passing common mode aggressors, such as mains frequencies, and thereby enables the common mode aggressors to be suppressed without affecting the desired differential mode signals at the same frequency. Thus, the second cut-off frequency may be higher than the first cut-off frequency.

According to an embodiment, the low pass filters of the signal channel feedback loop and the reference channel feedback loop each comprise a transconductance amplifier and a capacitor, wherein each transconductance amplifier comprises a first and a second input connected to the respective output node of the signal channel amplifier or the reference channel amplifier and a reference voltage.

The transconductance amplifier and capacitor may thus provide low pass gm-C filters for each feedback loop. The gm-C filters may provide filter characteristics for common mode signals and may be adapted for common mode rejection.

The filter cut-off frequency of the gm-C filters may be high. Thus, small filter capacitances may be required, which may imply that use may be made of parasitic capacitors for the low pass filters.

According to an embodiment, each transconductance amplifier is connected to receive the same reference voltage.

This may ensure that filters are configured to provide a low pass filter in respect of a common mode signal of the input signals of the read-out signal channels and the reference channel.

According to an embodiment, each read-out signal channel comprises a first transimpedance stage connected between the output node of the signal channel amplifier and the first output of the read-out signal channel, and a second transimpedance stage connected between the output node of the reference channel amplifier and the second output of the read-out signal channel.

Hence, each read-out signal channel may be configured to output a first and a second output so as to provide a fully differential amplification of the input and reference signals.

According to an embodiment, the first input node of each signal channel amplifier is a non-inverting input and the second input node of each signal channel amplifier is an inverting input, and wherein the first input node of the reference channel amplifier is a non-inverting input and the second input node of the reference channel amplifier is an inverting input.

Thus, the input signals are provided to non-inverting inputs, while feedback is coupled to inverting inputs. Hence, negative feedback is provided in the amplifiers.

According to a second aspect, there is provided a sensor for sensing a biopotential signal, said sensor comprising: a plurality of electrodes, configured to contact a skin surface of a subject and configured to provide input signals and a reference signal; and a read-out circuitry according to any one of the preceding claims for providing a differential output from each read-out signal channel of the read-out circuitry.

Effects and features of this second aspect are largely analogous to those described above in connection with the first aspect. Embodiments mentioned in relation to the first aspect are largely compatible with the second aspect.

Thus, a sensor is provided with a plurality of electrodes for acquiring a multi-channel biopotential signal. The re-use of amplification of the reference channel for a plurality of channels implies that power consumption of the sensor may be limited.

According to an embodiment, the sensor further comprises a patch, which is configured to carry the plurality of electrodes and the read-out circuitry.

Thus, the sensor may be implemented in a patch, which may be suited for attachment to a subject so as to arrange the plurality of electrodes in a relation to the subject for acquiring the biopotential signals.

According to an embodiment, the patch comprises an adhesive surface, which is configured for being attached to a chest area of a subject for acquiring a multi-channel electrocardiogram, ECG, signal by the sensor.

Thus, the patch may be attached to position the electrodes in an appropriate relation to a subject. This implies that the sensor facilitates acquiring a multi-channel ECG.

Hence, a high quality multi-channel ECG may be acquired using a sensor with a small form factor for attachment to a subject. This implies that the sensor may be suitable for use of acquiring an ECG during daily life of a subject, so as to facilitate monitoring heart activity of the subject over a long period of time without affecting daily life of the subject.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

Detailed embodiments of the present inventive concept will now be described with reference to the drawings.

Figure 1:
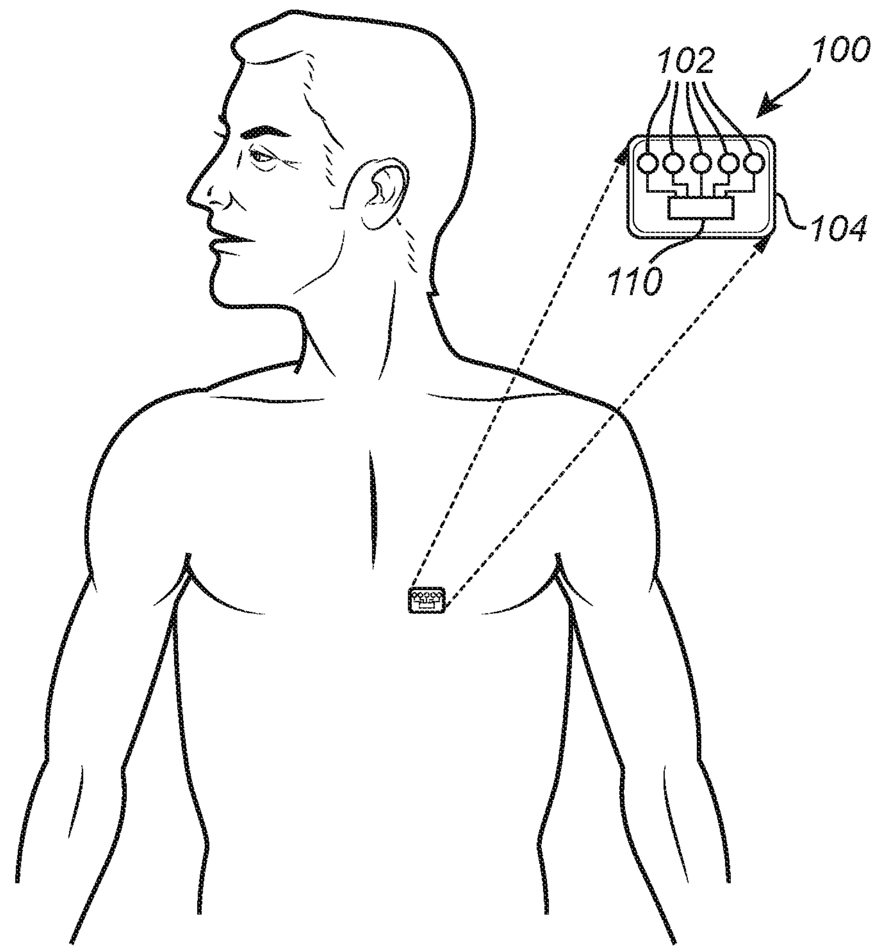
FIG. 1 is a schematic view of a sensor for sensing a biopotential signal according to an embodiment.

Referring now to FIG. 1, a sensor 100 for sensing a biopotential signal will be described.

The sensor 100 may comprise a plurality of electrodes 102. Each electrode 102 may be configured to be arranged in contact with a subject for acquiring a signal.

The electrodes 102 may e.g. be configured for direct galvanic contact with a skin of a person. However, it should also be realized that the electrodes 102 may be arranged within a carrier, so as to be arranged in close relation to the skin of the person for forming a capacitively coupled connection to the subject.

The electrodes 102 may be designed in many different ways as will be appreciated by a person skilled in the art. For instance, the electrodes 102 may comprise an area of conductive (e.g. metallic) material for acquiring of an electrical signal. The area of conductive material may be connected to a wire for transferring the electrical signal from the electrode 102.

The sensor 100 may comprise a carrier 104 which may be wearable by the subject. The carrier 104 may thus for instance comprise an adhesive patch for attachment to a skin surface of the subject. The carrier 104 may alternatively comprise a band element or ring-shaped element for attachment around a body part. The carrier 104 could for instance comprise two band parts, which may be attached to each other in an adjustable relationship for fitting the carrier 104 tightly around the body part, such as around a torso of the subject.

The electrodes 102 may be mounted in the carrier 104 so as to be arranged in a suitable relation to the subject, when the carrier 104 is attached or arranged on the subject.

The sensor 100 may be adapted for acquiring a biopotential signal. For instance, the sensor 100 may be configured for acquiring an electroencephalogram (EEG), an electrocardiogram (ECG) or an electromyogram (EMG). In the following, acquisition of an ECG will be mainly described, but it should be realized that the description of the sensor 100 may apply to acquisition of another biopotential signal instead.

The electrodes 102 may be mounted relatively close to each other in the carrier 104. In particular, for miniaturizing of the sensor 100, the carrier 104 should be small, which also implies that the electrodes 102 will be close to each other. Since the electrodes 102 are close to each other, ECG signals from a heart of the subject are not very different, which implies that a conventional ECG differential amplifier may only provide a small output signal and may also provide more or less the same signal for different channels. Hence, one of the electrodes 102 may be used as a common reference electrode for providing a reference signal, such that the signals for the other electrodes 102 are all differentially amplified in relation to the reference signal.

The sensor 100 may further comprise read-out circuitry 110 for acquiring a multi-channel biopotential signal from the electrodes 102, as will be described in further detail below. Each channel may provide fully differential amplification of the input signal of an electrode 102 in relation to the reference electrode.

The sensor 100 may thus acquire biopotential signals on a plurality of channels. The biopotential signals may be further processed in further processing circuitry of the sensor 100. For instance, the sensor 100 may comprise analog-to-digital converters (ADCs) for converting the acquired signals to digital representation.

The sensor 100 may further comprise a processing unit, which may be configured to process and/or analyze the acquired signals. The processing unit could for instance be configured to determine a heart rate from an acquired ECG or be configured to detect any abnormal events in heart activity.

The sensor 100 may further comprise a communication unit, which may be configured for wired and/or wireless communication with an external unit. Thus, the sensor 100 may be configured to transfer the acquired biopotential signals, possibly after further processing of the signals in the sensor 100, to an external unit, which may provide extensive analysis of the signals and/or enable presenting signals on a display.

Figure 2:
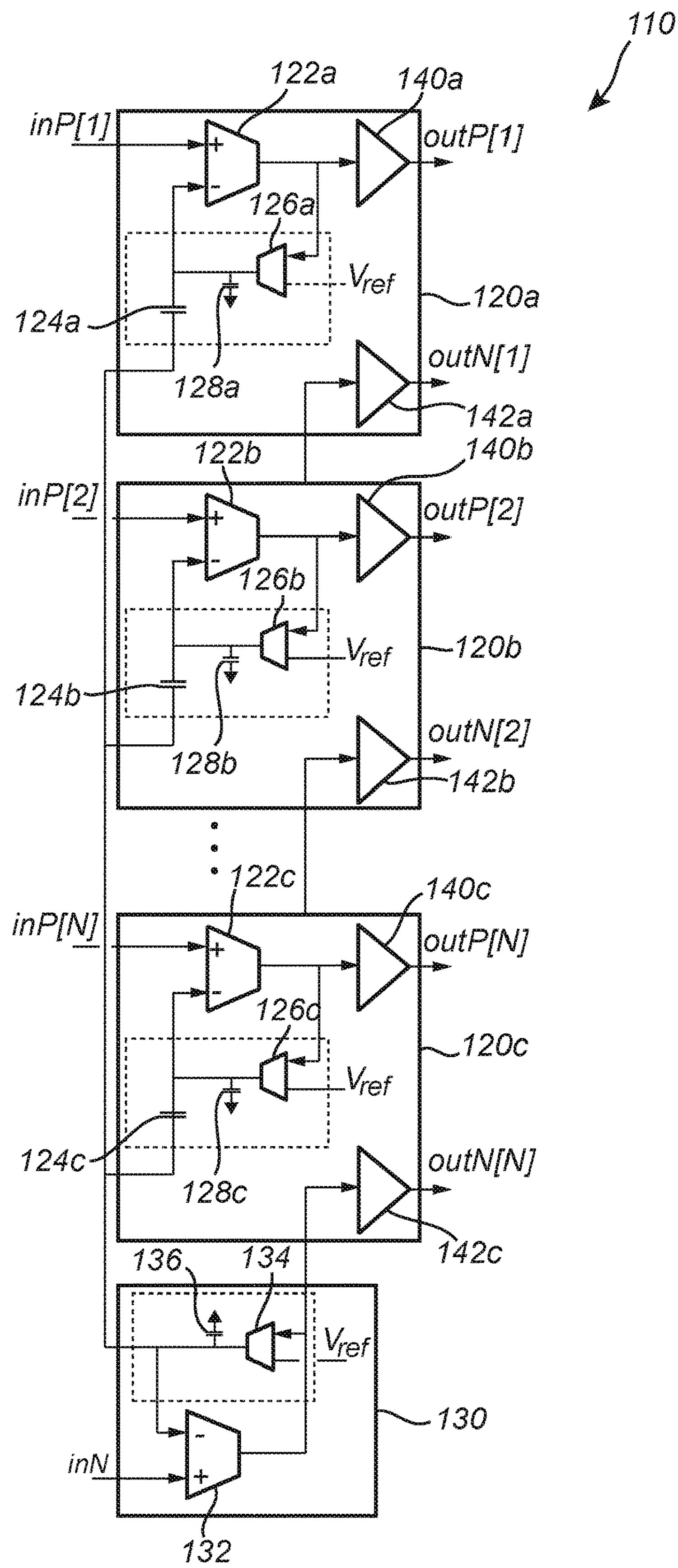
FIG. 2 is a schematic view of a read-out circuitry for acquiring a multi-channel biopotential signal according to a first embodiment.

Referring now to FIG. 2, a read-out circuitry 110 for acquiring a multi-channel biopotential signal from the electrodes 102 according to a first embodiment will be described.

The read-out circuitry 110 comprises a plurality of read-out signal channels 120*a-c*. Each signal channel 120*a-c* is configured to receive an input signal inP[1]-inP[N] from a unique signal electrode 102.

Each signal channel 120*a-c* comprises a signal channel amplifier 122*a-c*. The signal channel 120*a-c* may be configured to receive the input signal inP[1]-inP[N] on a first input node of the signal channel amplifier 122*a-c*. The first input node of the signal channel amplifier 122*a-c* may be a non-inverting input such that the signal channel 120*a-c* may be configured to receive the input signal inP[1]-inP[N] on a non-inverting input of the signal channel amplifier 122*a-c*.

The signal channel 120*a-c* may further comprise a signal channel feedback loop connecting an output node of the signal channel amplifier 122*a-c* to a second input node of the signal channel amplifier 122*a-c*. The feedback loop may be connected to an inverting input of the signal channel amplifier 122*a-c* to provide a negative feedback.

The read-out circuitry 110 may further comprise a reference channel 130, which is configured to receive a reference signal inN from a reference electrode, which acts as a common reference for each of the input signals inP[1]-inP[N] of the signal electrodes 102.

The reference channel may comprise a reference channel amplifier 132. The reference channel 130 may be configured to receive the reference signal inN on a first input node of the reference channel amplifier 132. The first input node of the reference channel amplifier 132 may be a non-inverting input such that the reference channel 132 may be configured to receive the reference signal inN on a non-inverting input of the reference channel amplifier 132.

The reference channel amplifier 132 may further comprise a reference channel feedback loop connecting an output node of the reference channel amplifier 132 to a second input node of the reference channel amplifier 132. The feedback loop may be connected to an inverting input of the reference channel amplifier 132 to provide a negative feedback.

The second input node of each signal channel amplifier 122*a-c* is connected to the second input node of the reference channel amplifier 132 via a capacitor 124*a-c* of each signal channel 120*a-c*.

The signal channel feedback loop and the reference channel feedback loop together form a feedback network. The signal channel feedback loop may comprise a low pass filter. The low pass filter may for instance be based on a transconductance amplifier 126*a-c* and a capacitor 128*a-c*. Also, the reference channel feedback loop may comprise a low pass filter. The low pass filter may for instance be based on a transconductance amplifier 134 and a capacitor 136. The low pass filters may provide a common mode filter characteristic of the feedback network.

In this regard, the transconductance amplifiers 126*a-c*, 134 may each be configured to receive a differential input based on the output from the signal channel amplifier 122*a-c*, 132 and a reference voltage.

Since the low pass filters are implemented in negative feedback loops, a high pass filter characteristic of the signal channel amplifiers 122*a-c* may be provided, providing DC offset cancellation.

The low pass filters may comprise a transconductor or transconductance amplifier 126*a-c*, 134 and a shunt capacitor 128*a-c*, 136. For common mode signals, the filters should pass a full frequency band of interest, thus including e.g. mains aggressors. This implies that a high cut-off frequency in respect of the common mode signals may be provided. Hence, the shunt capacitor 128*a-c*, 136 may be small and may, for example, be provided by parasitic capacitances of the transconductance amplifier 126*a-c*, 134.

The capacitor 124*a-c* may provide different filter responses for common mode and differential mode signals, as the capacitor 124*a-c* does not affect the common mode signals. Thus, the feedback network may be configured to provide a cut-off frequency in respect of differential signals, which is different from the cut-off frequency in respect of common mode signals. Thus, the feedback network may further be configured to provide DC offset cancellation.

Each read-out signal channel 120*a-c* may further comprise a first output connected to the output node of the signal channel amplifier 122*a-c* and a second output connected to the output node of the reference channel amplifier for providing a differential output of a first output signal outP[1]-outP[N] and a second output signal outN[1]-outN[N] by each read-out signal channel 120*a-c*.

The signal channel amplifiers 122*a-c* and the reference channel amplifiers 132 may be transconductance amplifiers. Each signal channel 120*a-c* may further comprise a first transimpedance amplifier 140*a-c* connected to the output node of the signal channel transconductance amplifier 122*a-c* and a second transimpedance amplifier 142*a-c* connected to the output of the reference channel transconductance amplifier 132. The signal channel 120*a-c* may hence act as an overall voltage amplifier.

Figure 3:
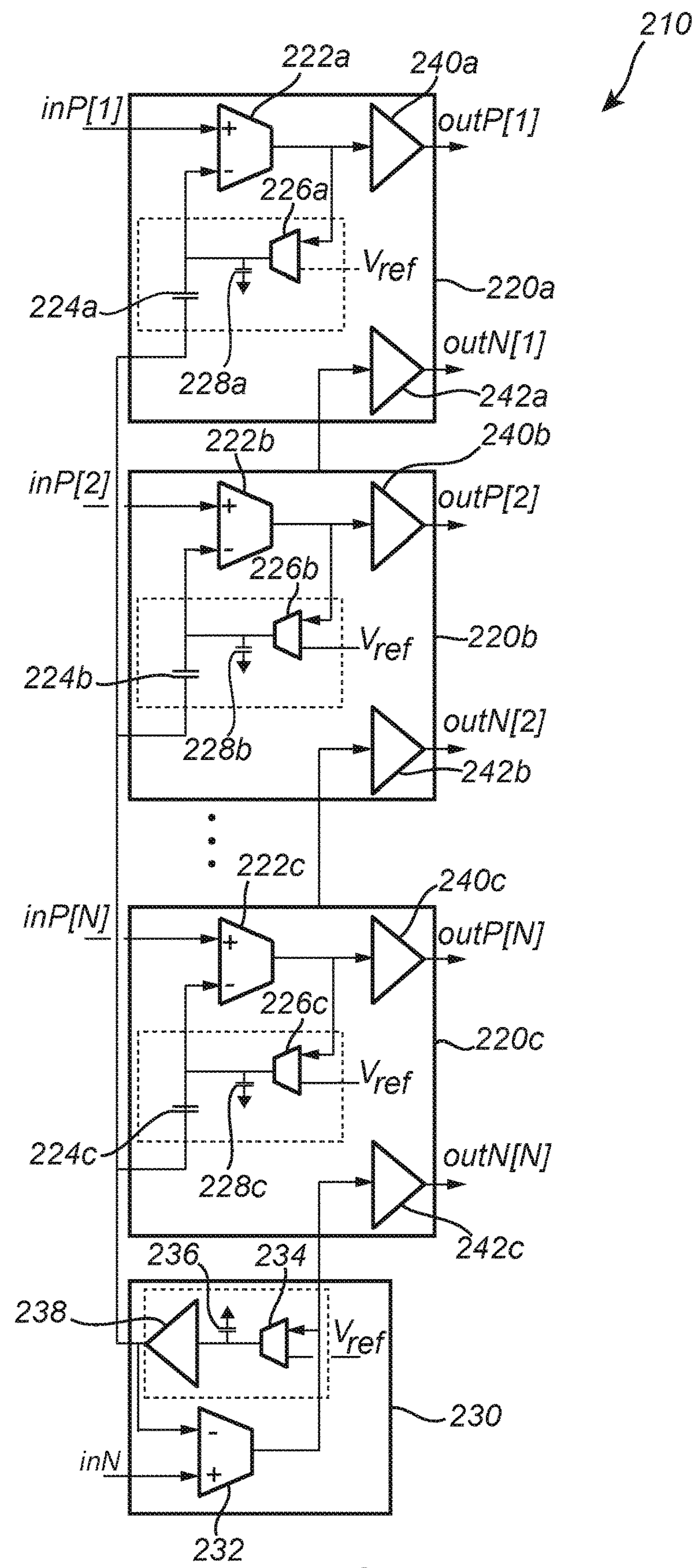
FIG. 3 is a schematic view of a read-out circuitry for acquiring a multi-channel biopotential signal according to a second embodiment.

Referring now to FIG. 3, a read-out circuitry 210 for acquiring a multi-channel biopotential signal from the electrodes 102 according to a second embodiment will be described.

The read-out circuitry 210 according to the second embodiment is in many aspects very similar to the read-out circuitry 110 according to the first embodiment. Thus, features of the read-out circuitry 210 of the second embodiment which are similar to the read-out circuitry 110 of the first embodiment will not be described in detail here.

The read-out circuitry 210 according to the second embodiment comprises a plurality of read-out signal channels 220*a-c* having signal channel amplifiers 222*a-c* which are configured to receive an input signal inP[1]-inP[N] on a first input node. The read-out circuitry 210 further comprises a reference channel 230 having a reference channel amplifier 232, which is configured to receive a reference signal inN. The signal channel amplifiers 222*a-c* and the reference channel amplifier 232 are provided with feedback loops to provide input on a second input node of the signal channel amplifiers 222*a-c* and the reference channel amplifier 232, respectively.

The second input node of each signal channel amplifier 222*a-c* is connected to the second input node of the reference channel amplifier 232 for providing a differential mode filter characteristic. Each signal channel and reference channel feedback loop further provides an active low pass filter (illustrated as a transconductance amplifier 226*a-c*, 234 and a shunt capacitor 228*a-c*, 236) having a cut-off frequency in respect of a common mode signal of the input signals inP[1]-inP[N] of the read-out signal channels 220*a-c* and the reference signal inN.

Each read-out signal channel 220*a-c* may further comprise a first transimpedance amplifier 240*a-c* connected to the output node of the signal channel amplifier 222*a-c* and a second transimpedance amplifier 242*a-c* connected to the output node of the reference channel amplifier 232 for providing a differential output of a first output signal outP[1]-outP[N] and a second output signal outN[1]-outN[N] by each read-out signal channel 220*a-c*.

In difference to the first embodiment, the read-out circuitry 210 of the second embodiment comprises a buffer 238 associated with the reference channel 232.

The buffer 238 may ensure that a low impedance node is provided in connecting the reference channel 230 to the signal channels 220*a-c*. Thanks to the buffer 238, a low impedance node may be provided to the capacitors 234. This may ensure that cross-talk between channels 220*a-c* is prevented so as to improve isolation between different signal channels 220*a-c*.

As illustrated in FIG. 3, the buffer 238 may be arranged within the reference channel feedback loop. The buffer 238 may thus be arranged between the transconductance amplifier 234 and the second input node of the reference channel amplifier 232.

The buffer 238 may be implemented as an operational amplifier, e.g. as a unity gain operational amplifier. The unity gain operational amplifier may provide a high input impedance and a low output impedance, while providing an output voltage equal to an input voltage.

Figure 4:
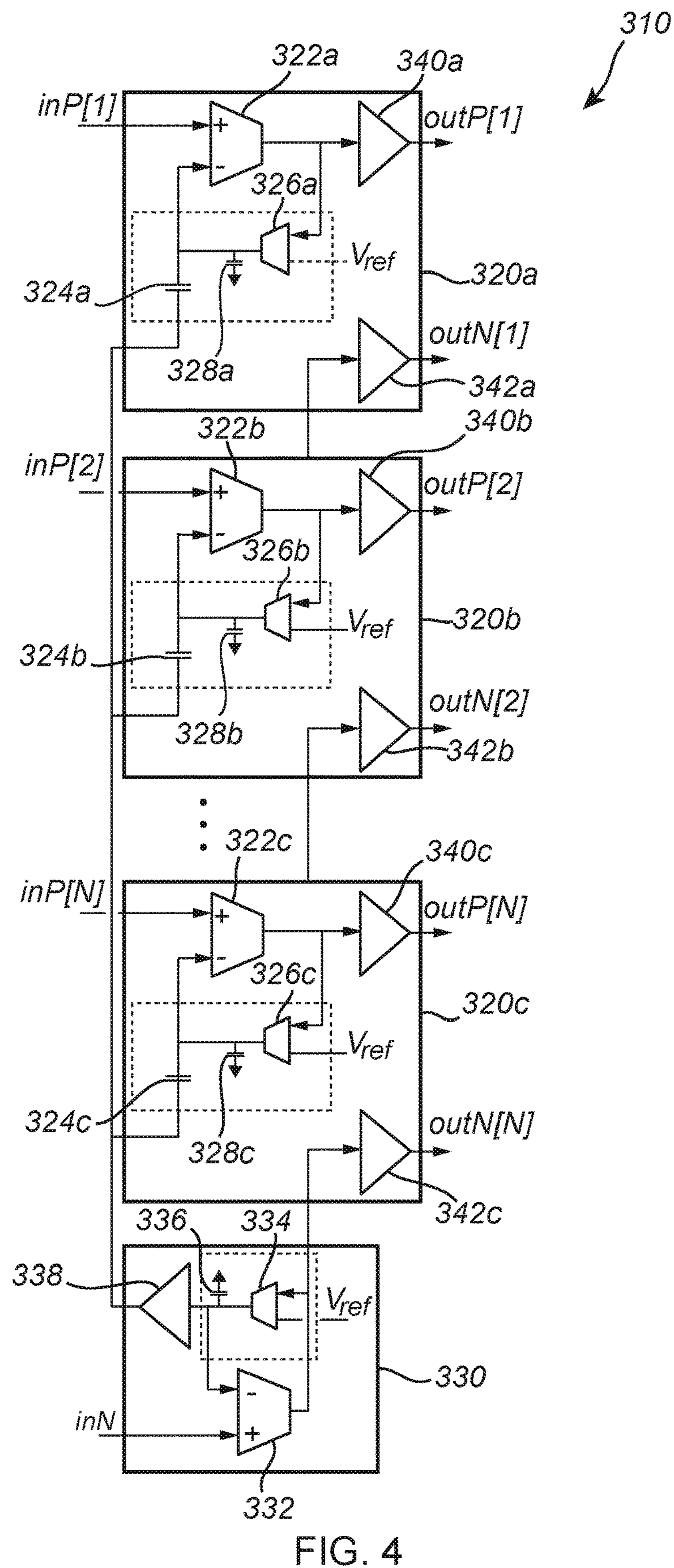
FIG. 4 is a schematic view of a read-out circuitry for acquiring a multi-channel biopotential signal according to a third embodiment.

Referring now to FIG. 4, a read-out circuitry 310 for acquiring a multi-channel biopotential signal from the electrodes 102 according to a third embodiment will be described.

The read-out circuitry 310 according to the third embodiment is in many aspects very similar to the read-out circuitries 110, 210 according to the first and second embodiments. Thus, features of the read-out circuitry 310 of the third embodiment which are similar to the read-out circuitries 110, 210 of the first and second embodiments will not be described in detail here.

The read-out circuitry 310 according to the third embodiment comprises a plurality of read-out signal channels 320*a-c* having signal channel amplifiers 322*a-c* which are configured to receive an input signal inP[1]-inP[N] on a first input node. The read-out circuitry 310 further comprises a reference channel 330 having a reference channel amplifier 332, which is configured to receive a reference signal inN. The signal channel amplifiers 322*a-c* and the reference channel amplifier 332 are provided with feedback loops to provide input on a second input node of the signal channel amplifiers 322*a-c* and the reference channel amplifier 332, respectively.

The second input node of each signal channel amplifier 322*a-c* is connected to the second input node of the reference channel amplifier 332 for providing a differential mode filter characteristic. Each signal channel and reference channel feedback loop further provides an active low pass filter (illustrated as a transconductance amplifier 326*a-c*, 334 and a shunt capacitor 328*a-c*, 336) having a cut-off frequency in respect of a common mode signal of the input signals inP[1]-inP[N] of the read-out signal channels 320*a-c* and the reference signal inN.

Each read-out signal channel 320*a-c* may further comprise a first transimpedance amplifier 340*a-c* connected to the output node of the signal channel amplifier 322*a-c* and a second transimpedance amplifier 342*a-c* connected to the output node of the reference channel amplifier 332 for providing a differential output of a first output signal outP[1]-outP[N] and a second output signal outN[1]-outN[N] by each read-out signal channel 320*a-c*.

Similar to the second embodiment, the read-out circuitry 310 of the third embodiment comprises a buffer 338 associated with the reference channel 332.

Again, the buffer 338 may ensure that a low impedance node is provided in connecting the reference channel 330 to the signal channels 320*a-c*. Thanks to the buffer 338, a low impedance node may be provided to the capacitors 334. This may ensure that cross-talk between channels 320*a-c* is prevented so as to improve isolation between different signal channels 320*a-c*.

In contrast to the second embodiment, the buffer 338 of the third embodiment of the read-out circuitry 310 is arranged outside the reference channel feedback loop. The buffer 338 may thus be arranged between the second input node of the reference channel amplifier 232 and the capacitors 224*a-c*.

The buffer 338 may be implemented as an operational amplifier, e.g. as a unity gain operational amplifier. The unity gain operational amplifier may provide a high input impedance and a low output impedance, while providing an output voltage equal to an input voltage.

Figure 5:
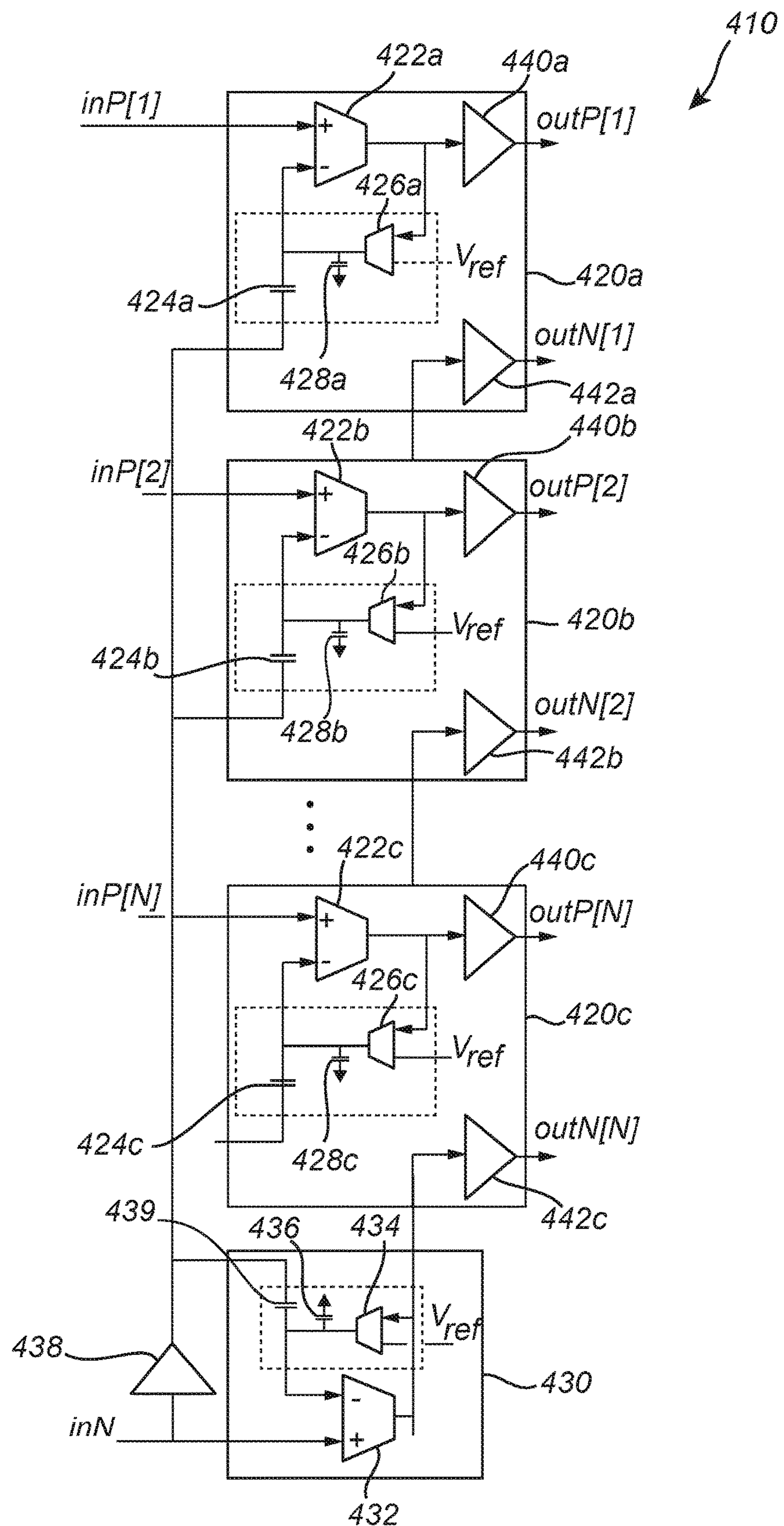
FIG. 5 is a schematic view of a read-out circuitry for acquiring a multi-channel biopotential signal according to a fourth embodiment.

Referring now to FIG. 5, a read-out circuitry 410 for acquiring a multi-channel biopotential signal from the electrodes 102 according to a fourth embodiment will be described.

The read-out circuitry 410 according to the fourth embodiment is in many aspects very similar to the read-out circuitries 110, 210, 310 according to the first, second, and third embodiments. Thus, features of the read-out circuitry 310 of the fourth embodiment which are similar to the read-out circuitries 110, 210, 310 of the first, second and third embodiments will not be described in detail here.

The read-out circuitry 410 according to the fourth embodiment comprises a plurality of read-out signal channels 420*a-c* having signal channel amplifiers 422*a-c* which are configured to receive an input signal inP[1]-inP[N] on a first input node. The read-out circuitry 410 further comprises a reference channel 430 having a reference channel amplifier 432, which is configured to receive a reference signal inN. The signal channel amplifiers 422*a-c* and the reference channel amplifier 432 are provided with feedback loops to provide input on a second input node of the signal channel amplifiers 422*a-c* and the reference channel amplifier 432, respectively.

The second input node of each signal channel amplifier 422*a-c* is connected to the second input node of the reference channel amplifier 432 for providing a differential mode filter characteristic. Each signal channel and reference channel feedback loop further provides an active low pass filter (illustrated as a transconductance amplifier 426*a-c*, 434 and a shunt capacitor 428*a-c*, 436) having a cut-off frequency in respect of a common mode signal of the input signals inP[1]-inP[N] of the read-out signal channels 420*a-c* and the reference signal inN.

Each read-out signal channel 420*a-c* may further comprise a first transimpedance amplifier 440*a-c* connected to the output node of the signal channel amplifier 422*a-c* and a second transimpedance amplifier 442*a-c* connected to the output node of the reference channel amplifier 432 for providing a differential output of a first output signal outP[1]-outP[N] and a second output signal outN[1]-outN[N] by each read-out signal channel 420*a-c*.

Similar to the second and third embodiments, the read-out circuitry 410 of the fourth embodiment comprises a buffer 438 associated with the reference channel 432.

Again, the buffer 438 may ensure that a low impedance node is provided in connecting the reference channel 430 to the signal channels 420*a-c*. Thanks to the buffer 438, a low impedance node may be provided to the capacitors 434. This may ensure that cross-talk between channels 420*a-c* is prevented so as to improve isolation between different signal channels 420*a-c*.

In the fourth embodiment, the buffer 438 is arranged between the first input node of the reference channel amplifier 432 and the capacitors 424*a-c*.

Here, the first input node of the reference channel amplifier 432 is connected to the capacitors 424*a-c* via the buffer 438. Thus, the second input node of the reference channel amplifier 432 may not be directly coupled to the capacitors 424*a-c* and an additional capacitor 439 may need to be arranged between the second input node of the reference channel amplifier 432 and the output node of the buffer 438.

The buffer 338 may be implemented as an operational amplifier, e.g. as a unity gain operational amplifier. The unity gain operational amplifier may provide a high input impedance and a low output impedance, while providing an output voltage equal to an input voltage.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A read-out circuitry for acquiring a multi-channel biopotential signal, said read-out circuitry comprising:

a plurality of read-out signal channels, wherein each signal channel is configured to receive an input signal from a unique signal electrode;

a reference channel, which is configured to receive a reference signal from a reference electrode;

wherein each of the read-out signal channels comprises a signal channel amplifier having a first input node and a second input node and an output node, wherein the first input node of the signal channel amplifier is connected to receive the input signal from the signal electrode, and wherein the output node of the signal channel amplifier is connected to the second input node of the signal channel amplifier via a signal channel feedback loop;

wherein the reference channel comprises a reference channel amplifier having a first input node and a second input node and an output node, wherein the first input node of the reference channel amplifier is connected to receive the input signal from the reference electrode, and wherein the output node of the reference channel amplifier is connected to the second input node of the reference channel amplifier via a reference channel feedback loop;

wherein the second input node of each signal channel amplifier is connected to the second input node of the reference channel amplifier for providing a differential input to each signal channel amplifier and for sharing amplification of the reference signal between the signal channels;

wherein each signal channel amplifier comprises a capacitor between the second input node of the signal channel amplifier and the second input node of the reference channel amplifier, and wherein each signal channel feedback loop and the reference channel feedback loop comprise a filter; and wherein each read-out signal channel comprises a first output connected to the output node of the signal channel amplifier and a second output connected to the output node of the reference channel amplifier for providing a differential output by each read-out signal channel, wherein the filter of each signal channel and reference channel feedback loop is a low pass filter having a first cut-off frequency for a differential signal of the input signal of the read-out signal channel and the reference signal, and wherein each signal channel and reference channel feedback loop is an active low pass filter having a second cut-off frequency for a common mode signal of the input signals of the read-out signal channels and the reference signal, wherein the second cut-off frequency is higher than the first cut-off frequency.

2. The read-out circuitry according to claim 1, further comprising a buffer, wherein the buffer is implemented as an operational amplifier.

3. The read-out circuitry according to claim 1, further comprising a buffer, wherein the buffer is arranged within the reference channel feedback loop.

4. The read-out circuitry according to claim 1, further comprising a buffer, wherein the buffer is arranged between the second input node of the reference channel amplifier and the capacitors of the signal channel amplifiers.

5. The read-out circuitry according to claim 1, further comprising a buffer, wherein the buffer is arranged between the first input node of the reference channel amplifier and the capacitors of the signal channel amplifiers.

6. The read-out circuitry according to claim 5, wherein the second input node of the reference channel amplifier is connected to an output node of the buffer via a capacitor.

7. The read-out circuitry according to claim 1, wherein the low pass filters of the signal channel feedback loop and the reference channel feedback loop each comprise a transconductance amplifier and a capacitor, wherein each transconductance amplifier comprises a first and a second input connected to the respective output node of the signal channel amplifier or the reference channel amplifier and a reference voltage.

8. The read-out circuitry according to claim 7, wherein each transconductance amplifier is connected to receive the same reference voltage.

9. The read-out circuitry according to claim 1, wherein each read-out signal channel comprises a first transimpedance stage connected between the output node of the signal channel amplifier and the first output of the read-out signal channel, and a second transimpedance stage connected between the output node of the reference channel amplifier and the second output of the read-out signal channel.

10. The read-out circuitry according to claim 1, wherein the first input node of each signal channel amplifier is a non-inverting input and the second input node of each signal channel amplifier is an inverting input, and wherein the first input node of the reference channel amplifier is a non-inverting input and the second input node of the reference channel amplifier is an inverting input.

11. A sensor for sensing a biopotential signal, said sensor comprising:

a plurality of electrodes, configured to contact a skin surface of a subject and configured to provide input signals and a reference signal; and a read-out circuitry according to claim 1 for providing a differential output from each read-out signal channel of the read-out circuitry.

12. The sensor according to claim 11, further comprising a patch, which is configured to carry the plurality of electrodes and the read-out circuitry.

13. The sensor according to claim 12, wherein the patch comprises an adhesive surface, which is configured for being attached to a chest area of a subject for acquiring a multi-channel electrocardiogram, ECG, signal by the sensor.

14. A read-out circuitry for acquiring a multi-channel biopotential signal, said read-out circuitry comprising:

a plurality of read-out signal channels, wherein each signal channel is configured to receive an input signal from a unique signal electrode;

a reference channel, which is configured to receive a reference signal from a reference electrode;

wherein each of the read-out signal channels comprises a signal channel amplifier having a first input node and a second input node and an output node, wherein the first input node of the signal channel amplifier is connected to receive the input signal from the signal electrode, and wherein the output node of the signal channel amplifier is connected to the second input node of the signal channel amplifier via a signal channel feedback loop;

wherein the reference channel comprises a reference channel amplifier having a first input node and a second input node and an output node, wherein the first input node of the reference channel amplifier is connected to receive the input signal from the reference electrode, and wherein the output node of the reference channel amplifier is connected to the second input node of the reference channel amplifier via a reference channel feedback loop;

wherein the second input node of each signal channel amplifier is connected to the second input node of the reference channel amplifier for providing a differential input to each signal channel amplifier and for sharing amplification of the reference signal between the signal channels;

wherein each signal channel amplifier comprises a capacitor between the second input node of the signal channel amplifier and the second input node of the reference channel amplifier, and wherein each signal channel feedback loop and the reference channel feedback loop comprise a filter; and wherein each read-out signal channel comprises a first output connected to the output node of the signal channel amplifier and a second output connected to the output node of the reference channel amplifier for providing a differential output by each read-out signal channel, wherein a buffer is arranged between the second input node of the reference channel amplifier and the capacitors of the signal channel amplifiers.

15. A read-out circuitry for acquiring a multi-channel biopotential signal, said read-out circuitry comprising:

a plurality of read-out signal channels, wherein each signal channel is configured to receive an input signal from a unique signal electrode;

a reference channel, which is configured to receive a reference signal from a reference electrode;

wherein each of the read-out signal channels comprises a signal channel amplifier having a first input node and a second input node and an output node, wherein the first input node of the signal channel amplifier is connected to receive the input signal from the signal electrode, and wherein the output node of the signal channel amplifier is connected to the second input node of the signal channel amplifier via a signal channel feedback loop;

wherein the reference channel comprises a reference channel amplifier having a first input node and a second input node and an output node, wherein the first input node of the reference channel amplifier is connected to receive the input signal from the reference electrode, and wherein the output node of the reference channel amplifier is connected to the second input node of the reference channel amplifier via a reference channel feedback loop;

wherein the second input node of each signal channel amplifier is connected to the second input node of the reference channel amplifier for providing a differential input to each signal channel amplifier and for sharing amplification of the reference signal between the signal channels;

wherein each signal channel amplifier comprises a capacitor between the second input node of the signal channel amplifier and the second input node of the reference channel amplifier, and wherein each signal channel feedback loop and the reference channel feedback loop comprise a filter; and wherein each read-out signal channel comprises a first output connected to the output node of the signal channel amplifier and a second output connected to the output node of the reference channel amplifier for providing a differential output by each read-out signal channel, wherein a buffer is arranged between the first input node of the reference channel amplifier and the capacitors of the signal channel amplifiers.

* * * * *